United States Patent [19]
Moy et al.

[11] Patent Number: 5,569,037
[45] Date of Patent: Oct. 29, 1996

[54] IMPLANT FIXTURE

[75] Inventors: Peter K. Moy, Los Angeles, Calif.; Kiyoshi Watanabe, Tokyo, Japan

[73] Assignee: GC Corporation, Tokyo, Japan

[21] Appl. No.: 306,313

[22] Filed: Sep. 15, 1994

[30] Foreign Application Priority Data

Sep. 17, 1993 [JP] Japan .................. 5-253675

[51] Int. Cl.$^6$ ........................................ A61C 8/00
[52] U.S. Cl. .............................. 433/173; 433/172
[58] Field of Search .......................... 433/172, 173, 433/174, 175, 176

[56] References Cited

U.S. PATENT DOCUMENTS 4,575,340  3/1986  Lustig .......................... 433/173
4,988,298  1/1991  Lazzara et al. ................ 433/73

Primary Examiner—Cary E. O'Connor
Attorney, Agent, or Firm—Oblon, Spivak, McClelland, Maier & Neustadt, P.C.

[57] ABSTRACT

An implant fixture is built up of a titanium body, a titanium cover that is threadedly engaged with the body, a support having a columnar form of protuberance to be loosely fitted into a small hole in the head of the cover, and a connector spring member including a cylindrical body having spring action that enables it to take hold of the outer surface of the cover through a flange provided at one end. A forceps is built up of two frames, each provided at one end with a finger ring having a claw and at the other end with a holding surface for holding a second shaft of the support in parallel with the axial direction, and a guide rod which extends axially from one frame and has a slidable weight.

5 Claims, 3 Drawing Sheets

IMPLANT FIXTURE

BACKGROUND OF THE INVENTION

The present invention relates to an implant fixture that functions as a combined retainer and stabilizer for a prosthesis filled and fixed in a cavity formed in the bone of toothless gums, and an implant fixture forceps which enables the implant fixture to be easily fitted in the cavity formed in the bone.

Generally, prosthetic dentistry has so far been carried out with bridges and dentures.

However, a problem with the bridge prosthetic dentistry is that sound natural teeth on both sides of a toothless gum site are cut to form a pier and a prosthesis is fixed on a metal member to engage the pier at a position corresponding to the toothless gum site; it is not only required to cut sound teeth, but deossification is also induced at the position corresponding to the toothless gum site, since no direct occlusal pressure is applied on the prosthesis at that position.

In denture prosthetic dentistry, a denture made of synthetic resin and the like is used as a prosthesis, and occlusal force acting on the prosthesis is born by remaining natural teeth and/or the mucosa of the mouth. Consequently, there are some grave defects such as a feeling of physical disorder to the prosthesis used, degradation of the taste as a result of taste receptors scattered among the mucosal tissue of the mouth being covered with the denture, and absorption of the alveolar ridge during an extended use of the prosthesis.

To eliminate these problems, a dental implant procedure has been developed and put to practical use, according to which an implant fixture that functions as a combined retainer and stabilizer for prostheses is fitted and fixed in a cavity formed in the bone of toothless gum sites to serve as the roots of natural teeth, and is provided with a prosthesis retainer to which a prosthesis is fixedly attached.

This dental implant procedure has one advantage of eliminating a feeling of physical disorder to the prosthesis used or degradation of the taste; achieving a feeling of use similar to that of natural teeth, because the prosthesis can be fixed without covering the mucosa of the mouth. Another advantage is that it is possible to minimize deossification that might be induced with no implant fixture fitted, because a suitable occlusal force is imparted to the jawbone. For these reasons, the dental implant procedure has showed a rapid progress to such an extent that it is now applicable to gum sites with one tooth or two or more teeth extracted or otherwise lost, and anodontia.

In the dental implant procedure, however, there is need of a surgical operation in which the bone of the toothless gum site is provided with a cavity to receive the implant fixture, and the implant fixture is fitted in the cavity followed by suture of the surrounding gum of the cavity. Thus, the implant fixture must conform to aseptic and uncontaminative conditions, and has not only good bondability to the jawbone when fitted in the cavity but also good bio-affinity.

In most cases, the dental implant procedure is usually carried out by a dual-operation manner comprising a first operation for forming a cavity in the jawbone of a toothless gum site and fitting an implant fixture in the cavity to have a sufficient bond to the jawbone, and a second operation in which, after the recovery of the surgically operated site, the gum site on the intra-oral side of the cavity is again incised to fix on the intra-oral side of the cavity an abutment that provides a mount for a prosthesis retainer. At the first operation, a pre-operation is needed, in which a cover is attached to the implant fixture to close up a threaded hole for fixing the abutment on the intra-oral side of the implant fixture and so prevent the penetration of the bone. Thus, the cover is attached to the implant fixture by threaded engagement within the threaded hole formed in the intra-oral side of the implant fixture.

Care must be taken in fitting the implant fixture in the cavity. This is because when the implant fixture is fitted too deeply in the cavity, the jawbone grows to the intra-oral side of the cover; at the second operation it is required to incise not only the epithelial gum but the cured bone as well, and when the fitting depth of the implant fixture into the cavity is too shallow, the suture of the epithelial gum is difficult, since the cover is located too deeply in the intra-oral side. Especially when the portion of the implant fixture to be fitted in the bone is in a columnar form, the fitting of the implant fixture into cavity formed in the bone of a toothless gum site is usually carried by press fitting. However, the as-formed cavity is relatively labile, it is required that press fitting take place in an accurate direction at a reasonable pressure.

An object of the present invention is to provide an implant fixture that can be easily fitted in a cavity formed in the bone of a toothless gum site with no damage to the cavity, and an implant fixture forceps that enables the implant fixture to be easily fitted in a cavity formed in the bone in an aseptic, uncontaminative yet safe manner.

SUMMARY OF THE INVENTION

According to one aspect of the invention, there is provided an implant fixture comprising in combination:

an implant fixture body of titanium having a nearly hemispheric head and a nearly columnar form contiguous to the head, a titanium cover having an externally threaded portion formed in a projected manner at one end thereof for threaded engagement with an internally threaded portion of implant fixture body and has a head provided with a small hole together with a groove for receiving a screwdriver at the other end thereof, an implant fixture support which is made up of a columnar form of protuberance at one end, which is to be loosely fitted in the small hole in the head of the cover, a columnar flange to which the protuberance is attached, a first shaft which is contiguous to the flange and has an outer diameter smaller than that of the flange, an intermediate flange which is contiguous to the first shaft and has an outer diameter larger than that of the first shaft, a second shaft which is contiguous to the flange and has an outer diameter smaller than the flange, and a round head which is contiguous to the second shaft and has an outer diameter larger than that of the second shaft, and a connector spring member including a cylindrical body flattened on one side for engagement with the flange of the implant fixture support, and having spring action that enables the outer surface of the cover to be held through the flange, a hollow of the cylindrical body being fitted over the first shaft of the implant fixture support, and a portion of the cylindrical body that holds the outer surface of the cover being provided with a plurality of slits.

Preferably, the implant fixture body is provided on the side with a plurality of grooves extending in the axial direction.

Preferably, the nearly hemispheric head of the implant fixture body and the outer surface of the body contiguous thereto are satinized.

Preferably, the cover is of a truncated conical shape.

Preferably, the end of the other side of the cylindrical body opposite to the flat portion of the connector spring member is outwardly folded back.

According to another aspect of the invention, there is provided an implant fixture forceps built up of two frames, each provided at one end with a finger ring and at the other end with a holding surface of a semicircular shape in section, which takes hold of the second shaft of the implant fixture support in parallel with the axial direction, said finger rings being provided with claws which engage each other, and the one end of one frame there is an axially extending guide rod at the one end of one frame, which has two stoppers with a slidable weight located therebetween.

BRIEF DESCRIPTION OF THE DRAWINGS

The implant fixture and implant fixture forceps according to the present invention will now be explained at great length, by way of example but not by way of limitation, with reference to the accompanying drawings, in which.

DETAILED EXPLANATION OF THE INVENTION

Figure 1:
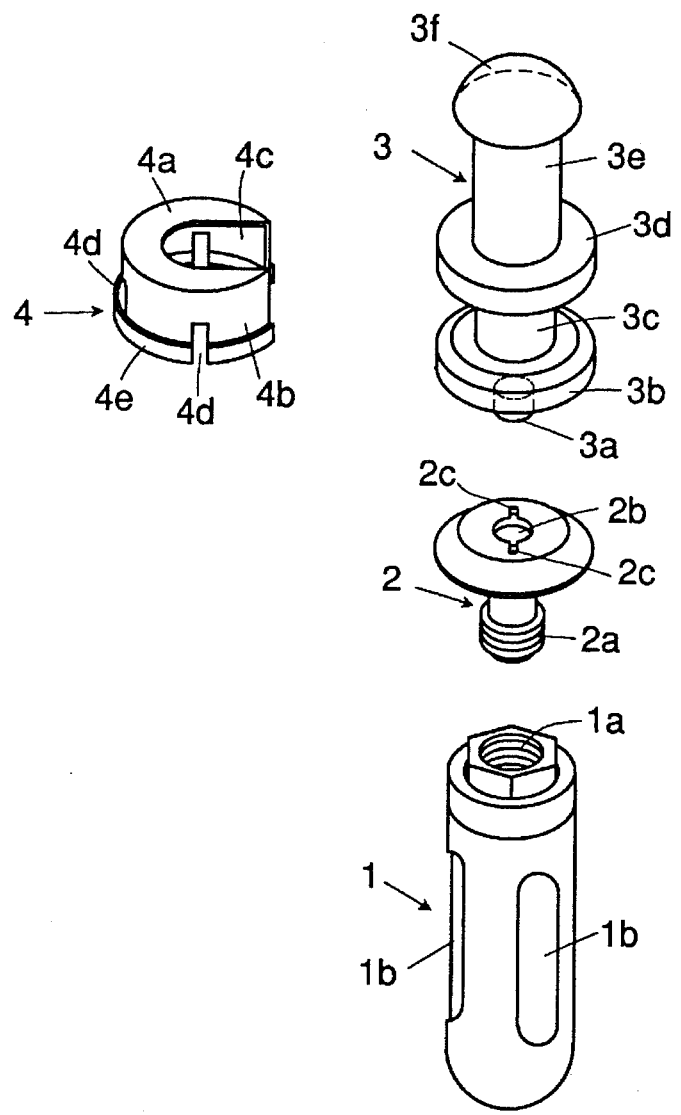
FIG. 1 is an exploded perspective view of the implant fixture according to the present invention.
Figure 2:
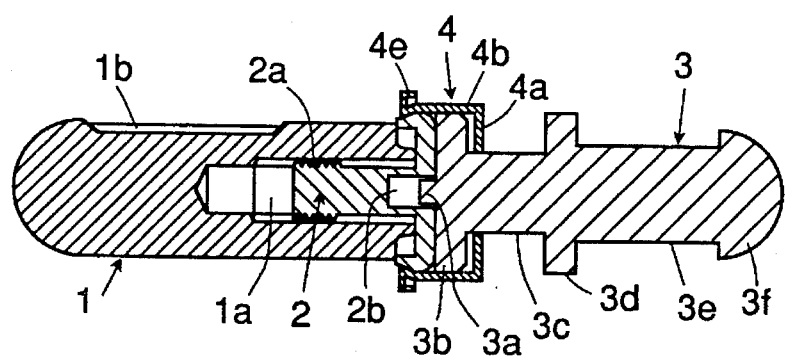
FIG. 2 is a sectional view of the implant fixture built up according to the present invention.
Figure 3:
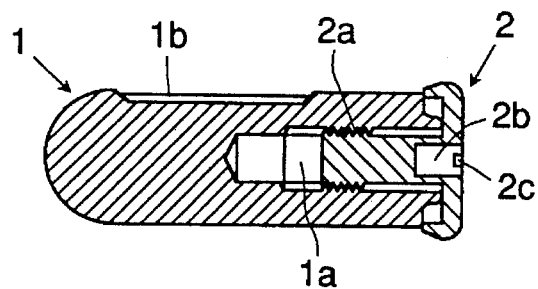
FIG. 3 is a sectional view of a covered implant fixture body, i.e., the implant fixture according to the present invention from which a connector spring member and an implant fixture support are removed.

An implant fixture body 1 of titanium has a nearly hemispheric head and a nearly columnar form contiguous to the head. The nearly columnar form includes at the end a connector that prevents any turning of an abutment to which a prosthesis retainer is attached, and is provided with an internal thread 1a. The prosthesis retainer is attached to the portion of the implant fixture body 1 that is inserted in the mouth. Although the connector is shown to project from the end of the body, it is understood that the connector may be retracted in the body. As shown, the body 1 may be provided with a plurality of axial grooves 1b, or may be so satinized so that the area of the outer surface with the bone in a cavity in the toothless gum can be increased.

A titanium cover 2 is externally threaded at 2a for threaded engagement with the internal thread 1a of the body while it is in no engagement with the connector spring member and has a head provided with a small hole 2b together with a groove 2c for receiving a screwdriver (a minus screwdriver in the embodiment illustrated), when the cover 2 is removed from the implant fixture body 1. Preferably, the cover 2 is of a substantially truncated cone shape; its outer diameter increases as it is spaced away from the implant fixture body 1, with the proviso that the portion of the cover 2 that faces the implant fixture body 1 has nearly the same outer diameter as that of the end thereof. With a properly controlled depth, the implant fixture body 1 with the cover 2 according to the invention can be fitted in a cavity formed in the bone of the toothless gum, because the inside of the head of the cover 2 abuts against the intra-oral bone in the cavity. The hole 2b in the head of the cover 2 must be small-enough to reduce as much as possible the amount of the gum entering that hole 2b. In the dual-surgical procedure, the intra-oral side of the cover 2 is covered with the gum after the first operation.

An implant fixture support 3 is made up of a columnar form of protuberance 3a at one end, which is to be loosely fitted in the small hole 2b in the head of the cover, a columnar flange 3b to which the protuberance 3a is attached, a first shaft 3c which is contiguous to the flange 3b and has an outer diameter smaller than that of the flange 3b, an intermediate flange 3d which is contiguous to the first shaft 3c and has an outer diameter larger than that of the first shaft 3c, a second shaft 3e which is contiguous to the flange 3d and has an outer diameter smaller than the flange 3d, and a round head 3f which is contiguous to the shaft 3e and has an outer diameter larger than that of the shaft 3e.

In a connector spring member 4, a cylindrical body 4b is flattened at 4a on one side for engagement with the flange 3b of the implant fixture support 3, and has spring action that enables the outer surface of the cover 2 to be held through the flange 3b. A hollow 4c of the cylindrical body 4b is fitted over the first shaft 3c of the implant fixture support 3, while a portion of the cylindrical body 4b that takes hold of the outer surface of the cover 2 is provided with a plurality of slits 4d. Preferably, the end of the other side of the cylindrical body 4b is outwardly folded back at 4e. When the implant fixture body 1 with the cover 2 according to the invention is fitted in a cavity formed in the bone of the toothless gum, this folded-back end 4e does not come into contact with the bone or the gum on the intra-oral side of the cavity; it does not cause damage to the bone or the gum. Besides, upon engagement with the bone on the intra-oral side of the cavity, the folded-back end 4e automatically disengages the cylindrical body 4b from the cover 2. To stabilize the engagement of the cylindrical body 4b with the outer surface of the cover 2, it is also desired that the end 4e of the body 4b be bent somewhat inwardly from the portion contiguous to the portion of the cover 2 having the maximum outer diameter.

Figure 4:
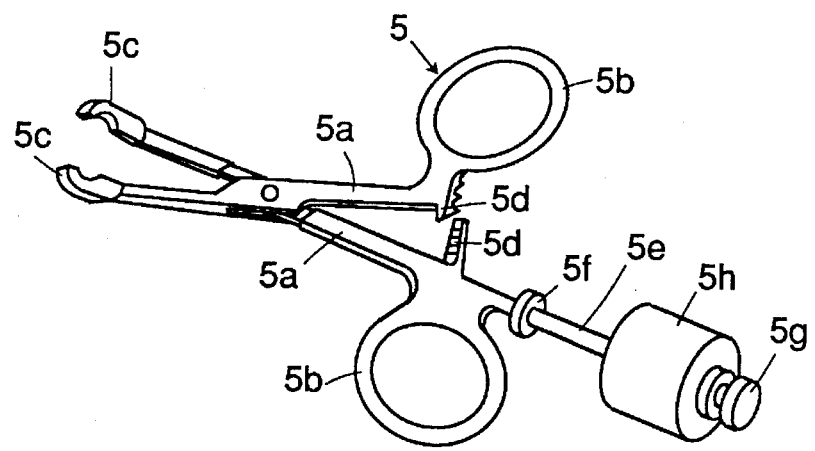
FIG. 4 is a perspective view of the implant fixture forceps according to the present invention.
Figure 5:
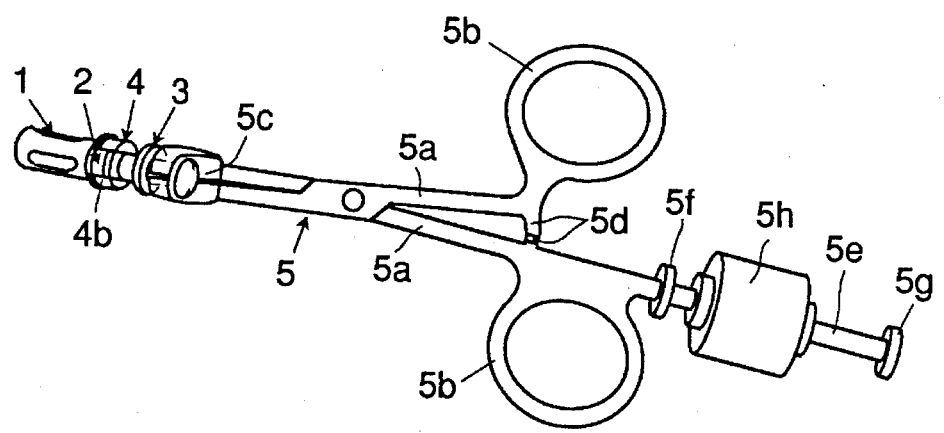
FIG. 5 is a perspective view of the present implant fixture being held by the present implant fixture forceps.
Figure 6:
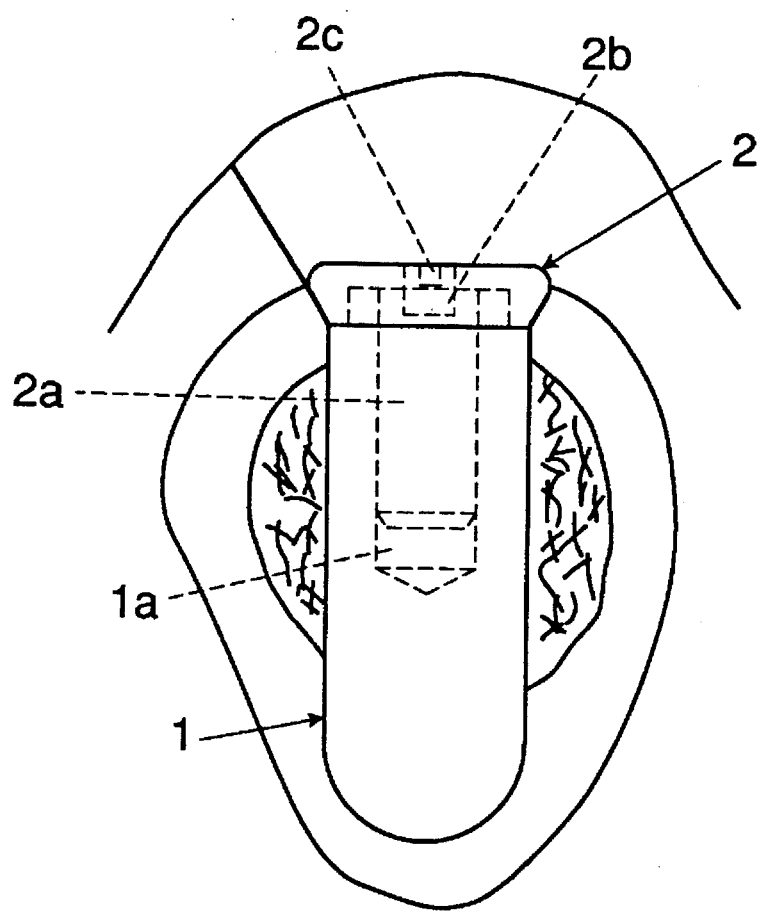
FIG. 6 is an enlarged sectional view of one post-treatment state wherein the covered implant fixture body is filled in a hole formed in a bone in the toothless gum.

As shown in FIG. 4, an implant fixture forceps 5 according to the invention is built up of two frames 5a, each provided at one end with a finger ring 5b and at the other end with a holding surface 5c of a semicircular shape in section, which takes hold of the second shaft 3e of the implant fixture support 3 in parallel with the axial direction. The finger rings 5b are formed with claws 5d which engage each other. At the one end of one frame 5a there is an axially extending guide rod 5e having two stoppers 5f and 5g with a slidable weight 5h located between them.

Reference will now be made on how to fit the implant fixture body 1 having the cover 2, using the implant fixture forceps 5 of the invention.

First, the cover 2 is attached to the implant fixture body 1 by the engagement of the internal thread 1a of the body with the external thread 2a of the cover 2. Then, the protuberance 3a at one end of the implant fixture support 3 is loosely fitted into the small hole 2b in the cover 2, so that the hollow 4c of the connector spring member 4 is fitted over the first shaft 3c while the flat portion 4a of the connector spring member 4 is located on the side of the intermediate flange 3d. After this, the connector spring member 4 is moved on the shaft 3c until the flat portion 4a engages the flange 3b, thereby causing the connector spring 4 to take hold of the outer surface of the cover 2. In this way, the implant fixture according to the invention is set up.

Following sterilization, the implant fixture of the invention is encased or otherwise properly packed with a suitable packaging material, and is unpacked just before it is fitted in a cavity formed in the bone of the toothless gum.

As a case of a packing material for the implant fixture body 1 with the cover 2 set in, a preferred type of a case or a packing material is the one which is able to be taken out without being touched with a hand.

Following unpacking, the finger rings 5b of the forceps 5 are handled to take hold of the second shaft 3e of the implant fixture support 3 between the holding surfaces 5c of the forceps 5. Since the claws 5d of the finger rings 5b are engaged with each other, the implant fixture support 3 can be tightly held in place. Then, the weight 5h is moved up along the guide rod 5e toward the stopper 5g while the implant fixture body 1 is placed in a cavity formed in the bone of the toothless gum. Upon engagement with the stopper 5g, the weight 5h falls and collides with the stopper 5f, giving on the finger ring 5 an impact enough to properly fit the implant fixture body 1 in a cavity formed in the bone of the toothless gum.

As stated, it is preferable that the cover 2 is of a substantially truncated cone shape; its outer diameter increases as it is away from the implant fixture body 1, with the proviso that the portion of the cover 2 that faces the implant fixture body 1 has nearly the same outer diameter as that of the end thereof. With a properly controlled depth, the implant fixture body 1 with the cover 2 according to the invention can be fitted in a cavity formed in the bone of the toothless gum, because the inside of the head of the cover 2 abuts against the intra-oral bone in the cavity.

After the barrel of the implant fixture is fitted into the cavity, the forceps 5 is slightly tilted from the axis of the implant fixture, so that the connector spring 4 and implant fixture support 3 can be readily detached from the implant fixture body 1 having the cover 2 with no damage to the cavity. This is because the slits 4d in the cylindrical body 4b enable the cylindrical body 4b to be sprung open and disengaged from the cover 2.

As stated, it is preferable that the end of the other side of the cylindrical body 4b is outwardly folded back at 4e. When the implant fixture of the invention is fitted in a cavity formed in the bone of the toothless gum, this folded-back end 4e comes into contact with the bone around the intra-oral side of the cavity, so that the cylindrical body 4b can be sprung upon to the ready detachment of the connector spring member 4 and implant fixture support 3 from the implant fixture body 1 having the cover 2 with no damage to the cavity.

As set forth above, the implant fixture according to the invention can be used with safety, because both the implant fixture body to be fitted in a cavity formed in the bone of a toothless gum site and the cover are made of titanium that is found not only to have good bone bondability and bio-affinity but also to offer no problem in terms of mechanical properties. The cover and implant fixture body, which are portions to be fitted in the cavity, are made integral with each other. The covered implant fixture body, while it remains intact, is attached to the implant fixture support by means of the connector spring member, so that there is no fear of contamination with bacteria or other contaminants. Even when the connector spring member and implant fixture support are attached to the covered implant fixture body, the connector spring member and implant fixture support can be easily detached from the covered implant fixture body with no excessive load on the bone by the disengagement from the cover of the cylindrical body of the connector spring member. This is achieved by tilting the implant fixture support slightly with respect to the implant fixture body. Alternatively or preferably, the end edge of the cylindrical body of the connector spring member opposite to the flat portion thereof is so folded back that it can be fitted into the bone on the intra-oral side of the cavity.

Preferably, the implant fixture body is provided on the side with a plurality of grooves in the axial direction, or the outer surfaces of the hemispheric head and the barrel contiguous thereto are satinized. This then enables the implant fixture body fitted in the cavity to be more firmly bonded to the bone.

Preferably, the cover is of a truncated cone shape that enables the implant fixture body to be fitted in the cavity with a controlled depth, because the end of the cover that faces the implant fixture body is in engagement with the bone on the intra-oral side of the cavity.

Preferably, the end of the connector spring member opposite to the flat portion thereof is outwardly folded back. When the implant fixture is fitted in the cavity, there is no fear of damage to the bone or the gum around the intra-oral side of the cavity. Besides, the folded-back end engages the bone around the intra-oral side of the cavity, so that the cylindrical body can be disengaged from the cover. Thus, the covered implant fixture body to remain in the cavity can automatically be detached from the connector spring member and implant fixture support.

With the implant fixture forceps according to the present invention, it is possible to fit the covered implant fixture body of the implant fixture in a cavity formed in the bone of a toothless gum site while it remains intact. That is, the present forceps enables the implant fixture body to be carried to and press fitted into the cavity in an continuous stable operation, unlike conventional touchy implant procedures wherein the implant fixture is carried to the cavity with one tool and then fitted into the cavity with another tool. Also, there is no fear of contamination with bacteria or other contaminants, because the implant fixture body can be protected against the hand or tools until the fitting of the covered implant fixture body into the cavity is completed.

Unless otherwise handled, the implant fixture support remains engaged with the holding surfaces of the ends of the frames, because the figure rings of the frames engage each other through the claws. Thus, it is unlikely for the dentist to miss minute parts forming the implant fixture or for the patient to swallow up a missing part.

Besides, the operation for removing the implant fixture from the sterilized package, carrying it to a cavity formed in the bone of a toothless gum site and removing an unnecessary portion can be continuously carried out, so that the operation can be done simply and with safety.

The implant fixture and implant fixture forceps according to the invention make a great contribution to the dental field.

What is claimed is:

1. An implant fixture comprising in combination:
   an implant fixture body of titanium having a nearly hemispheric head and a nearly columnar form contiguous to the head;
   a titanium cover having an externally threaded portion formed in a projected manner at one end thereof for threaded engagement with an internally threaded portion of said implant fixture body, said titanium cover further having a head provided with a small hole together with a groove for receiving a screwdriver at the other end thereof;

an implant fixture support which is made up of a columnar form of protuberance at one end, which is to be loosely fitted in the small hole in the head of the cover, a columnar flange to which the protuberance is attached, a first shaft which is contiguous to the columnar flange and has an other diameter smaller than that of the columnar flange, an intermediate flange which is contiguous to the first shaft and has an outer diameter larger than that of the first shaft, a second shaft which is contiguous to the intermediate flange and has an outer diameter smaller than that of the intermediate flange, and a round head which is contiguous to the second shaft and has an outer diameter larger than that of the second shaft; and a connector spring member including a cylindrical body flattened on one side for engagement with the columnar flange of the implant fixture support, said connector spring member having a spring action which permits an outer surface of the cover to be held through the columnar flange, a hollow of the cylindrical body being fitted over the first shaft of the implant fixture support, and a portion of the cylindrical body that holds the outer surface of the cover being provided with a plurality of slits.

2. An implant fixture as claimed in claim 1, wherein the implant fixture body is provided on a side with a plurality of grooves extending in an axial direction.

3. An implant fixture as claimed in claim 1 or 2, wherein the nearly hemispheric head of the implant fixture body and the outer surface of the cylindrical body contiguous thereto are satinized.

4. An implant fixture as claimed in claim 1 or 2, wherein an end of a further side of the connector spring member opposite to the flattened one side is folded outwardly back over a portion of the further side of the connector spring member.

5. An implant fixture as claimed in claim 1 or 2, wherein the cover has an outer diameter on a portion which faces an end of the implant fixture body which is nearly the same as an outer diameter of the end of the implant fixture body, the outer diameter of the cover becoming larger in a direction away from the implant fixture body to form a truncated cone shape wherein the cover is of a truncated cone shape.

\* \* \* \* \*